(12) United States Patent
Arrizza et al.

(10) Patent No.: US 9,889,244 B2
(45) Date of Patent: Feb. 13, 2018

(54) SYSTEM AND METHOD FOR CONTROLLING VENOUS AIR RECOVERY IN A PORTABLE DIALYSIS SYSTEM

(71) Applicant: Fresenius Medical Care Holdings, Inc., Waltham, MA (US)

(72) Inventors: John Arrizza, Oceanside, CA (US); John Erik Michael Palmroos, San Diego, CA (US); Ernesto Trillanes de la Fuente, Jr., Aliso Viejo, CA (US); Nhan Viet Pham, Fountain Valley, CA (US); Barry Neil Fulkerson, Longmont, CO (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 231 days.

(21) Appl. No.: 14/972,464

(22) Filed: Dec. 17, 2015

(65) Prior Publication Data
US 2017/0173248 A1    Jun. 22, 2017

(51) Int. Cl.
| | | |
|---|---|---|
| *B01D 63/00* | (2006.01) | |
| *B01D 21/30* | (2006.01) | |
| *C02F 1/44* | (2006.01) | |
| *A61M 1/36* | (2006.01) | |
| *A61M 1/16* | (2006.01) | |

(52) U.S. Cl.
CPC ........ *A61M 1/3627* (2013.01); *A61M 1/1603* (2014.02); *A61M 1/3626* (2013.01); *A61M 2202/0413* (2013.01); *A61M 2205/18* (2013.01); *A61M 2205/3331* (2013.01); *A61M 2205/502* (2013.01)

(58) Field of Classification Search
CPC ................ A61M 2205/18; A61M 1/14; A61M 2205/502; A61M 1/3626; B01D 61/30; B01D 61/243
See application file for complete search history.

(56) References Cited

U.S. PATENT DOCUMENTS

| | | | | |
|---|---|---|---|---|
| 5,423,738 A | * | 6/1995 | Robinson ................ | A61M 1/34 604/28 |
| 8,137,553 B2 | * | 3/2012 | Fulkerson ........... | A61M 1/1696 210/234 |
| 2009/0120864 A1 | * | 5/2009 | Fulkerson ................ | A61M 1/16 210/198.1 |
| 2011/0005986 A1 | * | 1/2011 | Kelly .................. | A61M 1/1696 210/175 |
| 2011/0315611 A1 | * | 12/2011 | Fulkerson ........... | A61M 1/1696 210/96.2 |
| 2014/0277894 A1 | * | 9/2014 | Doyle ................ | G01C 21/3407 701/23 |
| 2017/0173248 A1 | * | 6/2017 | Arrizza ............... | A61M 1/3627 |
| 2017/0258975 A1 | * | 9/2017 | Fulkerson ........... | A61M 1/1601 |

* cited by examiner

Primary Examiner — Ana Fortuna
(74) Attorney, Agent, or Firm — Novel IP

(57) ABSTRACT

The present specification discloses a portable dialysis system comprising a mechanism that allows the user to accurately position an air bubble in a venous line, so that it can be safely removed. When an air bubble is detected, the system automatically runs the blood pump in a direction such that the air bubble is placed close to the extraction point on the venous line, from where it can safely be removed using a needleless syringe.

16 Claims, 8 Drawing Sheets

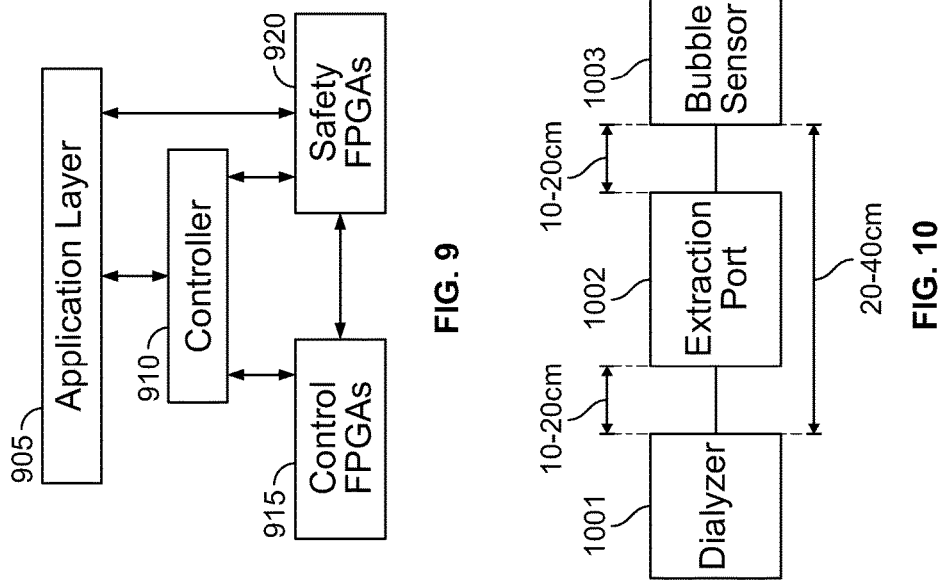
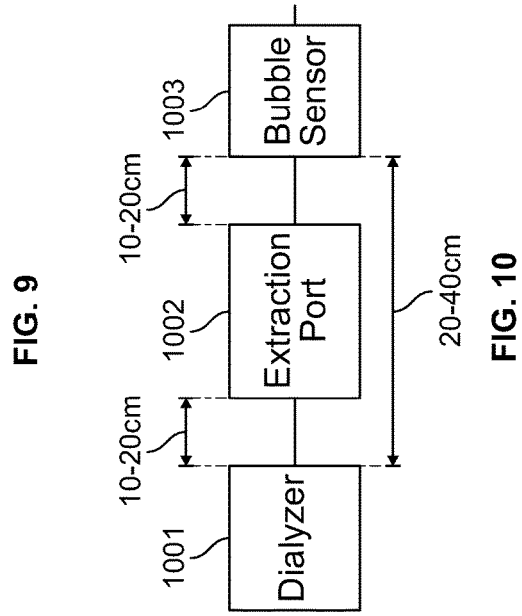
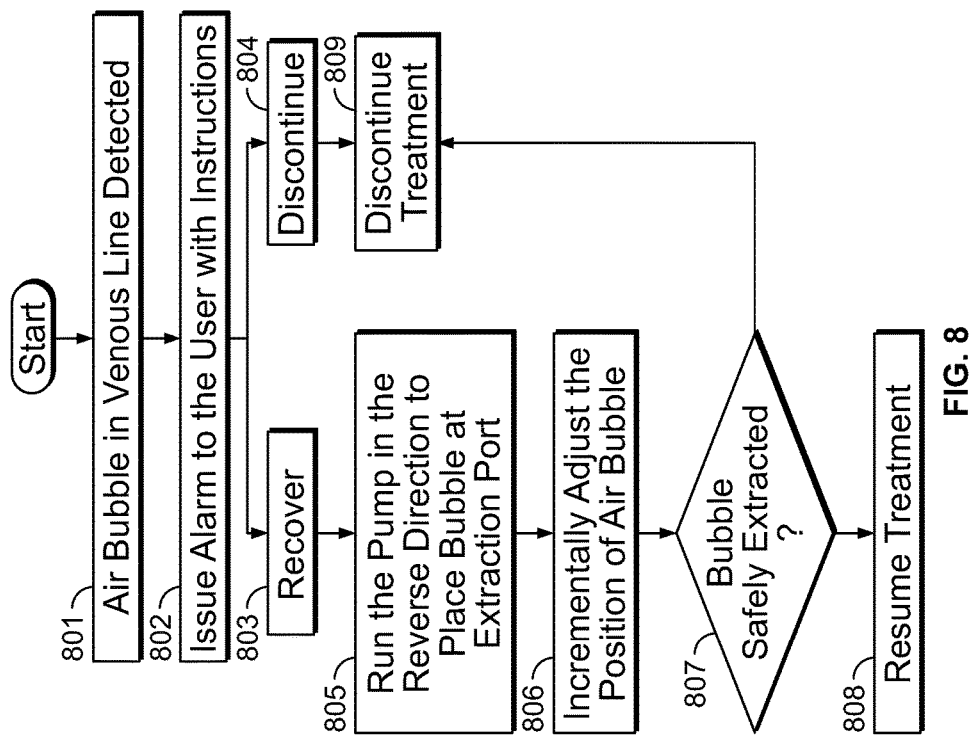

SYSTEM AND METHOD FOR CONTROLLING VENOUS AIR RECOVERY IN A PORTABLE DIALYSIS SYSTEM

FIELD

The present invention is directed towards dialysis systems, and particularly, to a portable dialysis system with an improved method for removing air bubbles from the venous bloodline during hemodialysis treatment.

BACKGROUND

Blood purification systems, which are used for conducting hemodialysis, hemodiafiltration or hemofiltration, involve the extracorporeal circulation of blood through an exchanger having a semi-permeable membrane. Such systems further include a hydraulic system for circulating blood and a hydraulic system for circulating replacement fluid or dialysate comprising the certain blood electrolytes in concentrations close to those of the blood of a healthy subject. Most of the conventionally available blood purification systems are, however, quite bulky in size and difficult to operate. Further, the design of these systems makes them unwieldy and not conducive to the use and installation of disposable components.

Standard dialysis treatment, using an installed apparatus in hospitals, comprises two phases, namely, (a) dialysis, in which toxic substances and scoriae (normally small molecules) pass through the semi-permeable membrane from the blood to the dialysis liquid, and (b) ultrafiltration, in which a pressure difference between the blood circuit and the dialysate circuit, more precisely a reduced pressure in the latter circuit, causes the blood content of water to be reduced by a predetermined amount.

Dialysis procedures using standard equipment tend to be cumbersome as well as costly, and generally require the patient to be bound to a dialysis center for long durations. While portable dialysis systems have been developed, conventional portable dialysis systems suffer from certain disadvantages. First, they are not sufficiently modular, thereby preventing the easy setup, movement, shipping, and maintenance of the systems. Second, the systems are not simplified enough for reliable, accurate use by a patient. The systems' interfaces and methods of using disposable components are subject to misuse and/or errors in usage by patients. For a portable dialysis system to be truly effective, it should be easily and readily used by individuals who are not health-care professionals, with the design of disposables and data input sufficiently constrained to prevent inaccurate use.

For example, one common problem encountered during a hemodialysis treatment is the appearance of an air bubble in the venous bloodline tubing going to the patient. An air bubble is detected typically by an occlusion detector in the system. Subsequently, the user (such as a technician/clinician or nurse) is required to move the air bubble to a different part of the tubing, where it can safely be removed. Typically, the bubble is positioned under a needleless port inline on the tubing for removal. Correct positioning of the air bubble is conventionally achieved with a push-hold-release mechanism, wherein the user presses, holds or releases a button repeatedly to move the bubble forward or backward until it reaches the desired position. Working with this kind of mechanism may prove complicated since the user may not have the dexterity or the reaction times necessary to move the air bubble quickly and accurately. This may result in a frustrating experience for the patient, besides being a potentially dangerous situation if the air bubble is not correctly removed.

Consequently, there is need for an improved apparatus and method for detecting and removing air bubbles in a venous line. Such a system should provide assistance to the user to accurately position the air bubble and simplify the process of air bubble removal.

SUMMARY

In some embodiments, the specification discloses a portable dialysis system comprising a mechanism for assisting a user in removing an air bubble that may be present in a patient's venous line during hemodialysis treatment. In one embodiment, the mechanism automatically moves the air bubble, such that it is placed close to an extraction point on the venous line, from where it can safely be removed using a needleless syringe.

In some embodiments, the specification discloses a portable dialysis system for conducting hemodialysis on a patient, the system comprising: an arterial blood line for carrying blood from the patient; a blood pump for drawing blood from said arterial line and pumping it to a dialyzer; a venous blood line for carrying purified blood from said dialyzer to said patient; a pinch clamp to prevent air in said venous line from being returned to the patient; an air bubble detector positioned in said venous blood line for detecting an air bubble arising in said venous blood line, wherein the air bubble detector is positioned within a range of 10 to 20 cm upstream of said pinch clamp and within a range of 20 to 40 cm downstream of said dialyzer; an extraction port located within a range of 10 to 20 cm upstream of said air bubble detector and within a range of 10 to 20 cm downstream of said dialyzer in the venous blood line, said extraction port being adapted to remove the said air bubble; and a controller in communication with said air bubble detector and said blood pump, said controller configured to cause said blood pump to run in a reverse direction back toward said dialyzer when an air bubble is detected, such that the air bubble is moved upstream towards the extraction port.

Optionally, the blood pump is run in a reverse direction for a specified time period.

Optionally, the system further comprises a display with a Graphical User Interface (GUI). Still optionally, the GUI is configured to issue an alarm as soon as an air bubble is detected. Still optionally, the GUI is configured to display instructions for a user to remove the air bubble. Still optionally, the GUI is configured to provide an option to the user to discontinue hemodialysis treatment when an air bubble is detected. Still optionally, the GUI is configured to display a plurality of navigation buttons, wherein said plurality of navigation buttons are configured to enable a user to adjust a position of the air bubble for extraction from said extraction port. Optionally, pressing at least one of said plurality of navigation buttons causes the blood pump to run in a forward or reverse direction, such that the air bubble is moved downstream or upstream towards the extraction port.

Optionally, said controller is configured to automatically run said blood pump in a reverse direction when an air bubble is detected.

Optionally, said controller is configured to operate said blood pump in a reverse direction on user input, when an air bubble is detected.

In some embodiments, the present specification discloses a method for removing an air bubble arising in a venous blood line in a portable dialysis system for conducting hemodialysis on a patient, said method comprising: detecting the air bubble arising in the venous blood line using an air bubble detector; issuing an alarm to the patient using a graphical user interface; electronically prompting a user of the portable dialysis system to select between recovering the air bubble and discontinuing treatment; and electronically receiving a selection of at least one recovering the air bubble or discontinuing treatment, wherein based upon said received selection, causing a blood pump to run in a reverse direction such that the air bubble is placed close to an extraction port; receiving input to confirm that the air bubble is successfully extracted; and resuming hemodialysis treatment when the user confirms the air bubble is successfully extracted.

Optionally, the method further comprises displaying a plurality of navigation buttons on said graphical user interface based upon electronically receiving the selection of recovering the air bubble. Still optionally, said at least one of said plurality of navigation buttons is configured to adjust a position of the air bubble for extraction from said extraction port. Still optionally, pressing a forward navigation button causes the blood pump to run in a forward direction such that the air bubble is moved downstream towards the extraction port. Still optionally, pressing a reverse navigation button causes the blood pump to run in a reverse direction such that the air bubble is moved upstream towards the extraction port.

Optionally, upon running the blood pump in the reverse direction, the blood pump operates for a first period of time of the order of 2-15 seconds, and at a rate of around 20-60 ml/min.

The aforementioned and other embodiments of the present specification shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 8 is a flowchart illustrating a process flow for air bubble detection and removal, according to one embodiment of the present specification;

FIG. 9 is a block diagram of exemplary hardware architecture of a dialysis system, according to one embodiment of the present specification; and FIG. 10 illustrates exemplary distances between various components of the dialysis circuit, according to one embodiment of the present specification.

DETAILED DESCRIPTION

Figure 1:
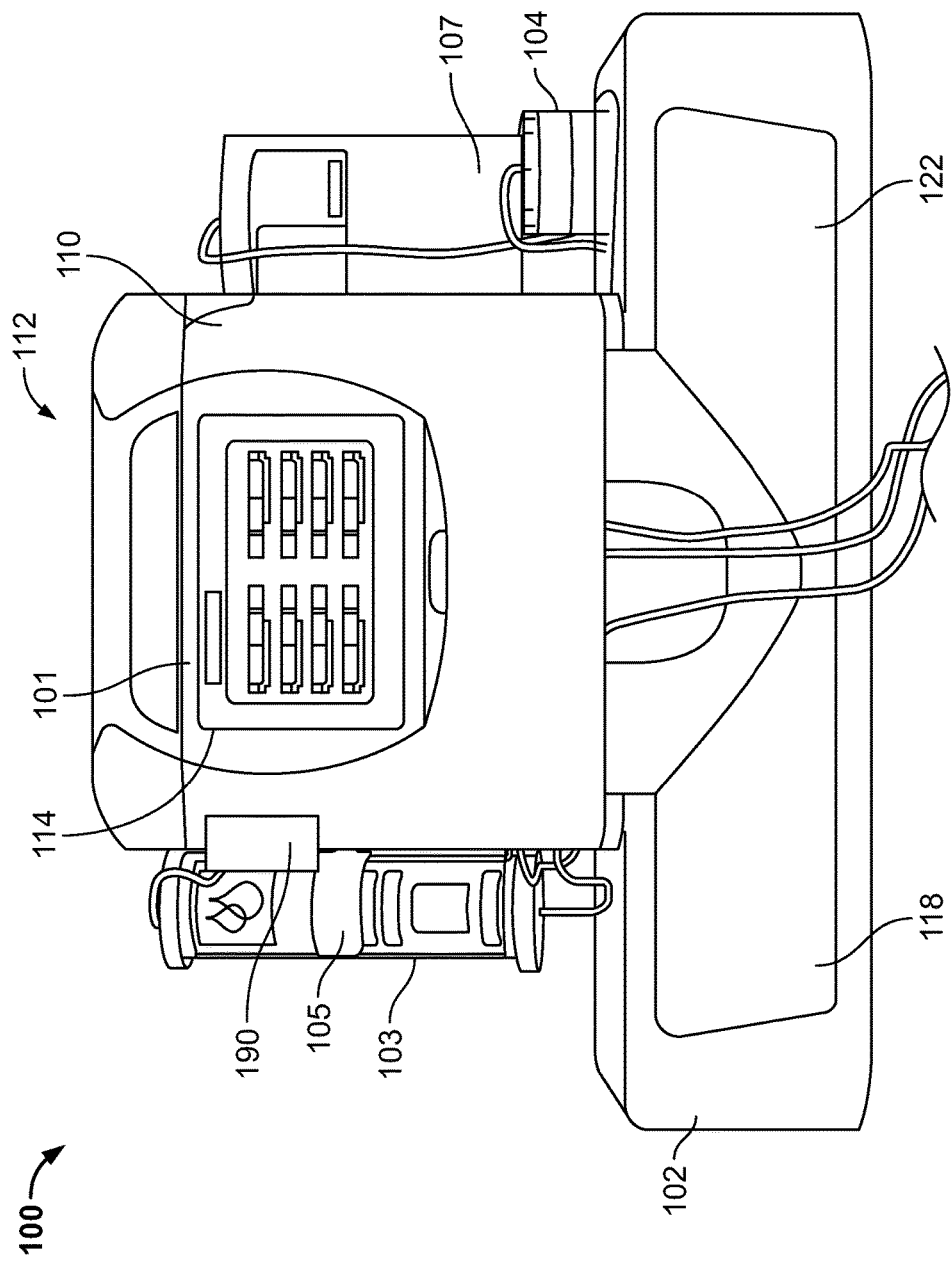
FIG. 1 is a front view of one embodiment of a portable dialysis system.

In one embodiment, the present specification describes a mechanism that allows the user of a portable dialysis system to accurately position an air bubble in a venous line, so that it can be safely removed. In one embodiment, the mechanism of the present specification allows for precise control of a blood pump in the portable dialysis system. Further, the mechanism of the present specification may be applied to any system that requires fluid to be positioned accurately within tubing.

While the present invention may be embodied in many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The term "and/or" means one or all of the listed elements or a combination of any two or more of the listed elements.

The terms "comprises" and variations thereof do not have a limiting meaning where these terms appear in the description and claims.

Unless otherwise specified, "a", "an", "the", "one or more", and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

FIG. 1 illustrates one embodiment of a portable dialysis system. Referring to FIG. 1, in one embodiment, the dialysis system 100 comprises a top unit 101 that is detachably affixed to a base 102. The base 102 comprises a reservoir 122 for fluid storage, measurement, and monitoring. The reservoir system 102 has a door 118 which, when pulled and not blocked by any protrusion, slides the reservoir 122 out, or otherwise makes the reservoir 122 accessible to a user, to allow a user to insert or change fluids used for dialysis. The top unit 101, also referred to as the main unit or controller unit, comprises a graphical user interface 114, pumping unit, and a door 110 with a power lock and mechanical backup mechanism, as further discussed below.

To a first side of the top unit 101 is a clasp 105 used to detachably affix a dialyzer 103. To a second, opposing side of the top unit 101 is a sorbent cartridge locking base 104 used to detachably affix a sorbent cartridge 107. It should be appreciated that the clasp 105, hemofilter 103, sorbent cartridge locking base 104 and sorbent cartridge 107 can be positioned on the same side of the top unit 101. In either case, the bottom unit has a sufficiently larger area relative to the top unit such that shelves are formed on either side of the top unit to hold the sorbent cartridge, to hold an infusate jar, to capture any spillage, and/or to channel any leaks into a leak detector.

In one embodiment, atop the controller unit 101 is a workspace in the form of a useable shelf 112.

Between the dialyzer 103 and door 110 are anti-coagulant pumps in the form of syringe pumps 190. Optionally, the top unit 101 can comprise a bottle holder that has a spiked base to receive a bottle, top-down, within the bottle holder housing. Infusion lines may be connected to the inlet of the blood pump, outlet of the blood pump, or outlet of the dialyzer (blood side). The infusion lines could also 'thread' through air bubble detectors to sense if/when the anti-coagulant is emptied or blocked.

Figure 2:
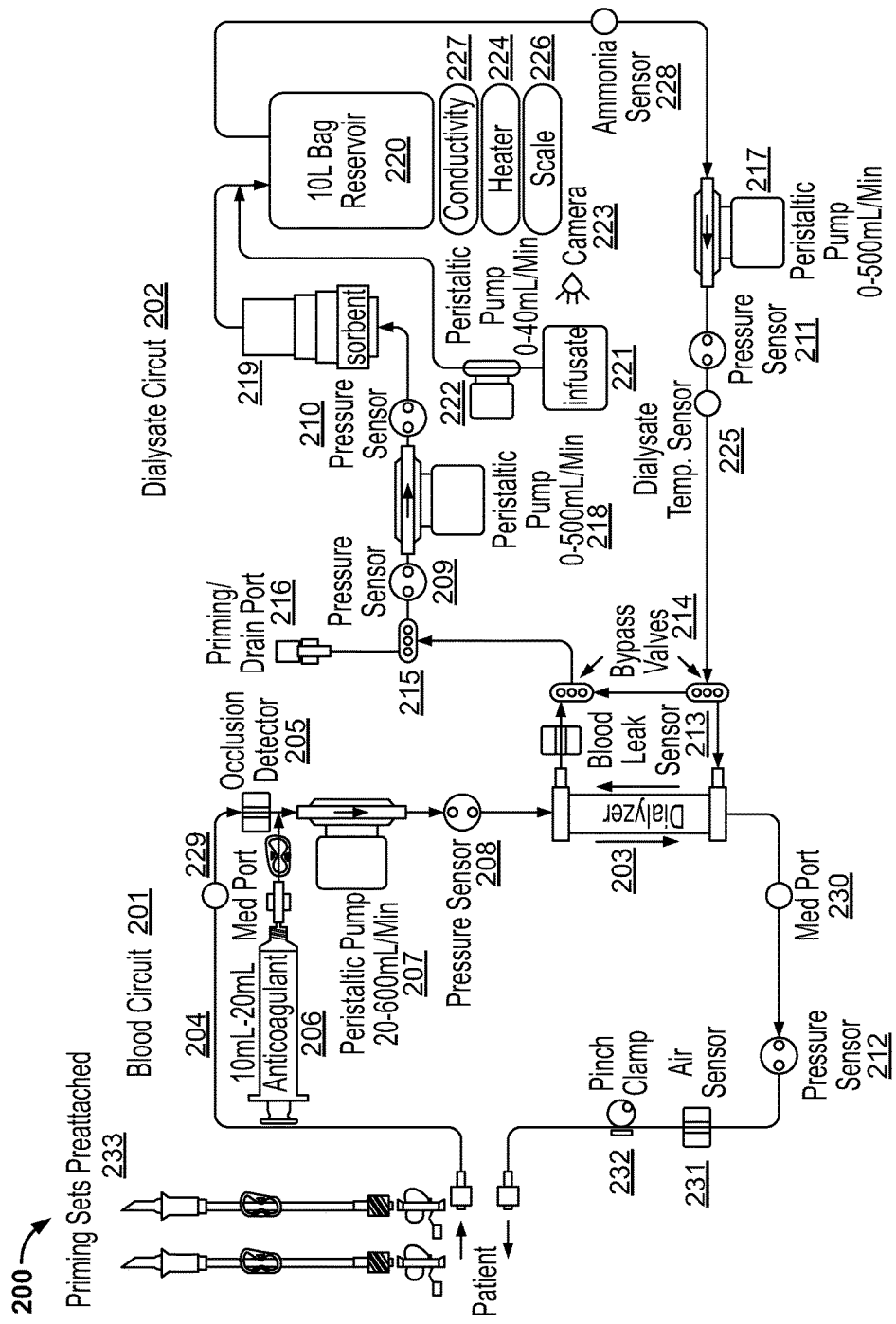
FIG. 2 is an exemplary fluid circuit diagram for a portable dialysis system.

FIG. 2 illustrates an exemplary fluidic circuit for an extracorporeal blood processing system 200 used for conducting hemodialysis and hemofiltration. In one embodiment of the present invention, the system 200 is implemented as a portable dialysis system which may be used by a patient for conducting dialysis at home. The hemodialysis system comprises two circuits—a Blood Circuit 201 and a Dialysate Circuit 202. Blood treatment during dialysis involves extracorporeal circulation through an exchanger having a semi permeable membrane—the hemodialyzer or dialyzer 203. The patient's blood is circulated in the blood circuit 201 on one side of the membrane (dialyzer) 203 and the dialysate, comprising the main electrolytes of the blood in concentrations prescribed by a physician, is circulated on the other side in the dialysate circuit 202. The circulation of dialysate fluid thus provides for the regulation and adjustment of the electrolytic concentration in blood.

The line 204 from the patient, which transports impure blood to the dialyzer 203 in the blood circuit 201, is provided with an occlusion detector 205 which is generally linked to a visual or audible alarm to signal any obstruction to the blood flow. In order to prevent coagulation of blood, delivery means 206, such as a pump, syringe, or any other injection device, for injecting an anticoagulant—such as heparin, into blood is also provided. A peristaltic pump 207 is also provided to ensure flow of blood in the normal (desired) direction.

A pressure sensor 208 is provided at the inlet where impure blood enters the dialyzer 203. Other pressure sensors 209, 210, 211 and 212 are provided at various positions in the hemodialysis system to track and maintain fluid pressure at desired levels at specific points within the respective circuits.

At the point where used dialysate fluid from the dialyzer 203 enters the dialysate circuit 202, a blood leak sensor 213 is provided to sense and warn of any leakage of blood cells into the dialysate circuit. A pair of bypass valves 214 is also provided at the beginning and end points of the dialysate circuit, so that under conditions of start-up, or at other times as deemed necessary by the operator, the dialyzer can be bypassed from the dialysate fluid flow, yet the dialysate fluid flow can still be maintained, i.e. for flushing or priming operations. Another valve 215 is provided just before a priming/drain port 216. The port 216 is used for initially filling the circuit with a dialysate solution, and to remove used dialysate fluid after, and in some instances during, dialysis. During dialysis, valve 215 may be used to replace portions of used dialysate with high concentrations of, for instance, sodium with replenishment fluid of appropriate concentration so that overall component concentration of the dialysate is maintained at a desired level.

The dialysate circuit is provided with two peristaltic pumps 217 and 218. Pump 217 is used for pumping dialysate fluid to the drain or waste container, as well as for pumping regenerated dialysate into the dialyzer 203. Pump 218 is used for pumping out spent dialysate from the dialyzer 203, maintaining fluid pressure through the sorbent 219, and pumping in dialysis fluid from port 216 to fill the system or maintain component concentration in the dialysate. In one embodiment, the motors of both the pumps are equipped with sensors to ensure the motor shaft is actually rotating when required.

A sorbent cartridge 219 is provided in the dialysate circuit 202. The sorbent cartridge 219 contains several layers of materials, each having a role in removing impurities, such as urea and creatinine. The combination of these layered materials allows water suitable for drinking to be charged into the system for use as dialysate fluid. It also allows closed loop dialysis. That is, the sorbent cartridge 219 enables regeneration of fresh dialysate from the spent dialysate coming from the dialyzer 203. For the fresh dialysate fluid, a lined container or reservoir 220 of a suitable capacity such as 0.5, 1, 5, 8 or 10 liters is provided.

Depending upon patient requirements and based on a physician's prescription, desired quantities of an infusate solution 221 can be added to the dialysis fluid. Infusate 221 is a solution containing minerals and/or glucose that help replenish minerals like potassium and calcium in the dialysate fluid at levels after undesired removal by the sorbent. A peristaltic pump 222 is provided to pump the desired amount of infusate solution 221 to the container 220. Alternatively, the infusate solution 221 can be pumped into the outflow line from reservoir 220. A camera 223 may optionally be provided to monitor the changing liquid level of the infusate solution as a safety check warning of infusate flow failure and/or function as a bar code sensor to scan bar codes associated with additives to be used in a dialysis procedure. Optionally, an ammonia sensor 228 may be provided.

A heater 224 is provided to maintain the temperature of dialysate fluid in the container 220 at the required level. The temperature of the dialysate fluid can be sensed by the temperature sensor 225 located just prior to the fluid's entry into the dialyzer 203. The container 220 is also equipped with a scale 226 for keeping track of the weight, and therefore volume, of the fluid in the container 220, and a conductivity sensor 227, which determines and monitors the conductivity of the dialysate fluid. The conductivity sensor 227 provides an indication of the level of sodium in the dialysate.

A medical port 229 is provided before blood from the patient enters the system for dialysis. Another medical port 230 is provided before clean blood from the dialyzer 203 is returned to the patient. An air (or bubble) sensor 231 and a pinch clamp 232 are employed in the circuit to detect and prevent any air, gas or gas bubbles from being returned to the patient.

Priming set(s) 233 is/are attached to the dialysis system 200 that help prepare the system by filling the blood circuit 201 with sterile saline before it is used for dialysis. Priming set(s) may consist of short segments of tubing with IV bag spikes or IV needles or a combination of both pre-attached.

One of ordinary skill in the art would infer from the above discussion that the exemplary fluidic circuits for a hemodialysis and/or hemofiltration system are complex. If implemented in a conventional manner, the system would manifest as a mesh of tubing and would be too complicated for a home dialysis user to configure and use. Therefore, in order to make the system simple and easy to use at home by a patient, in one embodiment the fluidic circuits are implemented in the form of a compact manifold in which most components of the fluidic circuit are integrated into a single piece of molded plastic or multiple pieces of molded plastic that are configured to connect together to form a single operative manifold structure.

Figure 3:
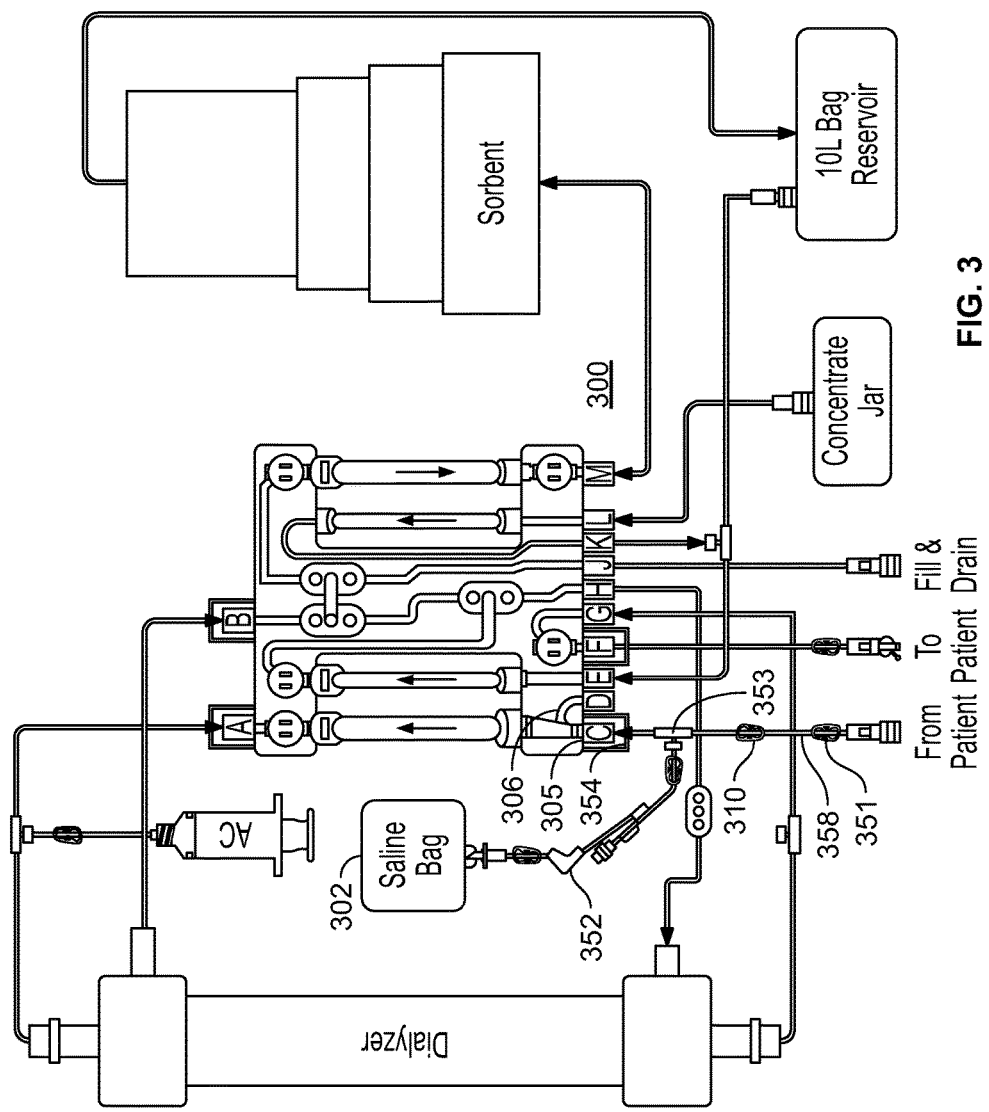
FIG. 3 is a schematic diagram of one embodiment of an exemplary manifold used with a hemodialysis system.

FIG. 3 is a schematic of one embodiment of an exemplary manifold 300, used with a hemodialysis system. Referring to FIG. 3, tube segments 358 are bonded into the compact manifold 300. A number of ports, such as C 305 and D 306 are provided in the manifold, which connect with tubes external to the manifold to allow the flow of various fluids in and out of the manifold. In one embodiment, various sensors, including optical sensors for sensing blood leakage, air bubbles, and/or occlusion are attached to, and around, pre-defined areas of the manifold. In the present example, the system is configured for a saline rinse back. Conventionally, a saline rinse back, which serves to flush the system with saline, is performed by detaching a tubular segment 358 that connects the dialysis blood circuit to the patient at connection 351 and attaching the tubular segment 358 to a saline source 302 via connection points 352 and 353. This conventional approach has disadvantages, however, including the breaching of a sterile connection. It should be appreciated that the connection points can be any form of connection, including luer connections, snap fits, needleless inserts, valves, or any other form of fluidic connection.

Another approach to a saline rinse back includes connecting the saline source 302 via connection point 352 to connection point 353, while maintaining the connection to the patient. While it avoids breaching the sterile connection, it exposes a patient to a saline fluid flow that may contain air bubbles. Because no air bubble detector is typically present in the tubular segment 358 between the point of saline connection 353 and the point of connection to the patient 351, there is a danger that an excessively large air bubble would form and, because there is no mechanism to detect such an air bubble and inform the patient, enter the patient's blood stream, causing substantial injury.

Alternatively, a preferred approach to performing a saline rinse back is to maintain the blood circuit connection between the patient and the dialysis system via tubular segment 358, which connects to the manifold 300 at port C 305 and the patient at connection point 351 and fluidically connect the saline source 302 to the manifold 300 at port D 306. With the patient still fluidically connected to the dialysis system, saline is permitted to flow, by gravity or applied pressure, into the manifold 300 via port D 306, which is adjacent to port C 305. The saline flow serves to flush the manifold 300 with saline and, in particular, to flow out of the manifold 300 via port C 305, through tubular segment 358, and into the patient via connection 351. An air bubble detector is present in region 354, proximate to port C 305. When the manifold 300 is installed in the controller unit and therefore adapted to detect air bubbles in fluid flow exiting port C 305, saline exiting the manifold 300 and toward the patient will be monitored for air bubbles, via the air bubble detector in region 354. If an air bubble is detected, an alarm will sound, thereby signaling to a user that he or she should either disconnect from the system or extract the air bubble, using a syringe, from access point 310. This method and system maintains a sterile connection while still monitoring and alarming for the presence of air bubbles.

Once an air bubble is detected, the user (such as a clinician or nurse) is required to move the air bubble to a different part of the tubing, where it can safely be removed. Typically, the bubble is positioned under a needleless port inline on the tubing, such as access point 310 for removal. In existing systems, a push-hold-release mechanism is provided for moving the air bubble, which comprises a button that the user presses, holds or releases a repeatedly to move the bubble is moved forward or backward until it reaches the desired position. In this mechanism, typically the amount of movement of the air bubble is determined by the user via the length of time the button is held down. When the user determines the movement is enough, they release the button. The tasks of keeping the button pressed for the correct length of time, releasing hold at just the right time and choosing the opposite motor direction and repeating steps if the air bubble has gone too far, may prove tedious and complicated for a user. Further, if the user is a patient or an elderly person, they may not have the dexterity or the reaction times necessary to move the air bubble accurately.

Thus, push-hold-release mechanism is complicated for users who may not be very precise, may be distracted, or may have cognitive impairment such that they can't hold and release correctly. A simpler and more accurate mechanism would be, for example, a one-press-one movement mechanism, such that pressing a button once moves the bubble by a specific amount, pressing the button again moves the bubble again, and so on.

The task of accurately positioning an air bubble is simplified in the system of present specification by automatically positioning the air bubble close to the desired location for removal, as soon as the air bubble is detected. Thereafter, the user is only required to make small incremental adjustments to bring the bubble to the exact position for removal.

Figure 4:
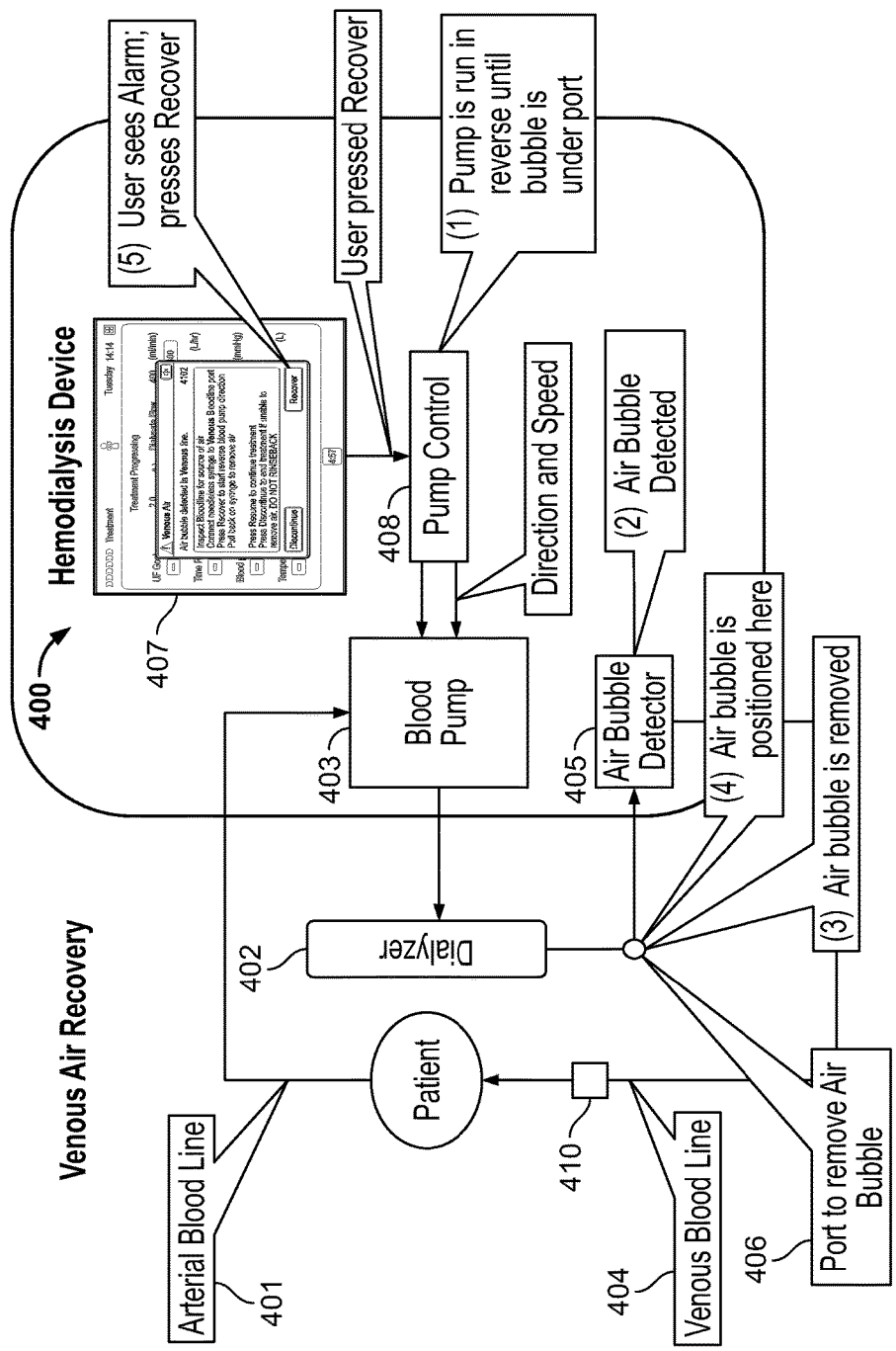
FIG. 4 is a flow diagram illustrating a process of air bubble detection and removal in a hemodialysis system, according to one embodiment of the present specification.

FIG. 4 is a diagram illustrating the mechanism of air bubble detection and removal in a hemodialysis system 400, according to one embodiment of the present specification. Referring to FIG. 4, during hemodialysis treatment, an arterial blood line 401 is used to carry impure blood from the patient 410 to the dialyzer 402. A peristaltic pump or blood pump 403 draws the patient's arterial impure blood along the arterial line 401 and pumps the blood through dialyzer 402. In one embodiment, the blood pump is connected to a pump control 408, which controls the direction and flow of the fluid (blood) through the pump. It may be noted that pump control refers to the software and algorithm used to drive the pump motor to achieve the expected fluid rate. In one embodiment, the pump control mechanism is controlled by low-level software, or firmware, which runs on the controller and receives inputs from the GUI. The controller and GUI have been earlier described with reference to FIG. 1. It may be appreciated that the pump control algorithm may be a simple one, which defines the speed of the motor (in RPM) to achieve a desired flow rate (in ml/min, for example), or it can be a complex one taking into account non-linearities and other factors that affect the flow rate. In one embodiment, the pump motor is a stepper and it is controlled by a series of pulses. As known in the art, each pulse moves the stepper motor one step. In one embodiment, an encoder is provided on the motor which is used for feedback and error detection.

Purified blood flows downstream from the dialyzer 402 and back to the patient through a venous blood line 404. An air bubble detector 405 is placed in the downstream path, in order to promptly detect any air bubble that may arise before it enters into the patient's blood stream. A pinch clamp or pinch valve 410 may also be employed in the circuit to prevent accumulated air from being returned to the patient. It may be noted that the pinch valve (also known as "Venous Clamp") is a safety feature that is used in the case of alarms, power failure, and other anomalous scenarios. It clamps the venous line shut to prevent air bubbles from reaching the patient in these scenarios.

An access point or a needleless port 406 is provided in the venous line tubing, from where the air bubble can be removed. In certain embodiments, the access point/port may be used to administer medicine to the patient.

The hemodialysis system 404 further comprises a display 407 having a GUI, as described earlier with reference to FIG. 1. In one embodiment, the display 407 comprises a touch screen capable of accepting tactile inputs from the user. Further, since it is important that the device be easy to use, especially in a home setting, maximal use of colors and the touch screen is provided for the application. In one embodiment, the touch screen allows multiple user input configurations, provides multiple language capability, and can be readily seen at night (particularly with brightness controls and night-vision colors). In one embodiment, when issuing alarms, alerts or reminders to the user, the GUI provides visual as well as audio signals.

Thus, if an air bubble is detected by the detector/sensor 405, an audible and/or visual alarm is issued by the GUI. The alarm is issued under instructions from the main control unit or controller (as mentioned earlier with reference to FIG. 1), which receives input from the air bubble detector. This alarm signals to the user that they should either disconnect from the system or extract the air bubble.

It may be noted that the pinch clamp 410 protects the patient, but also prevents the fluid from moving during air recovery. Therefore, the components in a hemodialysis system are ordered such that when the fluid is moving in normal course the bubble sensor is first in the stream (after the dialyzer), followed by the pinch clamp, and finally the patient. This ensures that when a bubble is detected, the pump is stopped and the pinch clamp is activated. The pinch clamp serves as a safety mechanism such that even if the pump fails to stop, the pinch clamp prevents the bubble from entering the patient. When the fluid is being moved for bubble extraction, the pinch clamp can be opened to allow the fluid to move. To ensure that the bubble does not reach the patient when the pinch clamp is open, the extraction point is placed upstream of the bubble sensor.

Referring simultaneously to FIG. 2 and FIG. 4, in one embodiment, the bubble sensor 231, 405, which may be of capacitive type, optical type or any other type suitable for the application is positioned 10 to 20 cm downstream of a dialyzer 203, 402 and 10 to 20 cm upstream of a pinch clamp 232, 410. In one embodiment, the air bubble sensor is placed 2 to 5 cm downstream of a pressure sensor 212. In another embodiment, the air bubble sensor is placed upstream of a pressure sensor 212. In one embodiment, at least one extraction port 230, 406 is positioned 10 to 20 cm upstream of the bubble sensor 231, 405 and 10 to 20 cm downstream of a dialyzer 203, 402. In one embodiment, the extraction port is placed 10 to 20 cm upstream of a pressure sensor 212. In another embodiment, the extraction port is placed 10 to 20 cm downstream of a pressure sensor 212.

FIG. 10 illustrates exemplary distances between various components of the dialysis circuit, according to one embodiment of the specification. Referring to FIG. 10, extraction port 1002 is placed about 10-20 cm downstream from the dialyzer 1001, and bubble sensor 1003 is placed about 10-20 cm further downstream from the extraction port 1001. Thus, in one embodiment, the bubble sensor 1003 is placed at a distance of about 20-40 cm downstream from the dialyzer 1001.

It may be noted the minimum distance the bubble sensor can be placed from the extraction point depends on a number of factors. For example, the distance should be enough to allow a user with average dexterity to successfully move the bubble to the extraction point. This would mean that the distance between the bubble sensor and the extraction point is at least 1.5-3.5 cm. Another factor is the response time of the bubble sensor and the amount of time taken to stop the pump after detection. Taking into account the speed at which the fluid is moving at the time of the detection, 1.5-3.5 cm again is the minimum distance. A person of ordinary skill in the art would, however, appreciate that 10 cm is a more reasonable lower bound. Further, for users who are elderly or dexterity impaired would be more comfortable with a slightly larger distance, such as up to 20 cm. It may also be noted that a 10-20 cm distance is also reasonable from the bubble sensor to the other components, as it would be difficult for a user to maneuver an extraction syringe in the region if the components are cramped.

Figure 5:
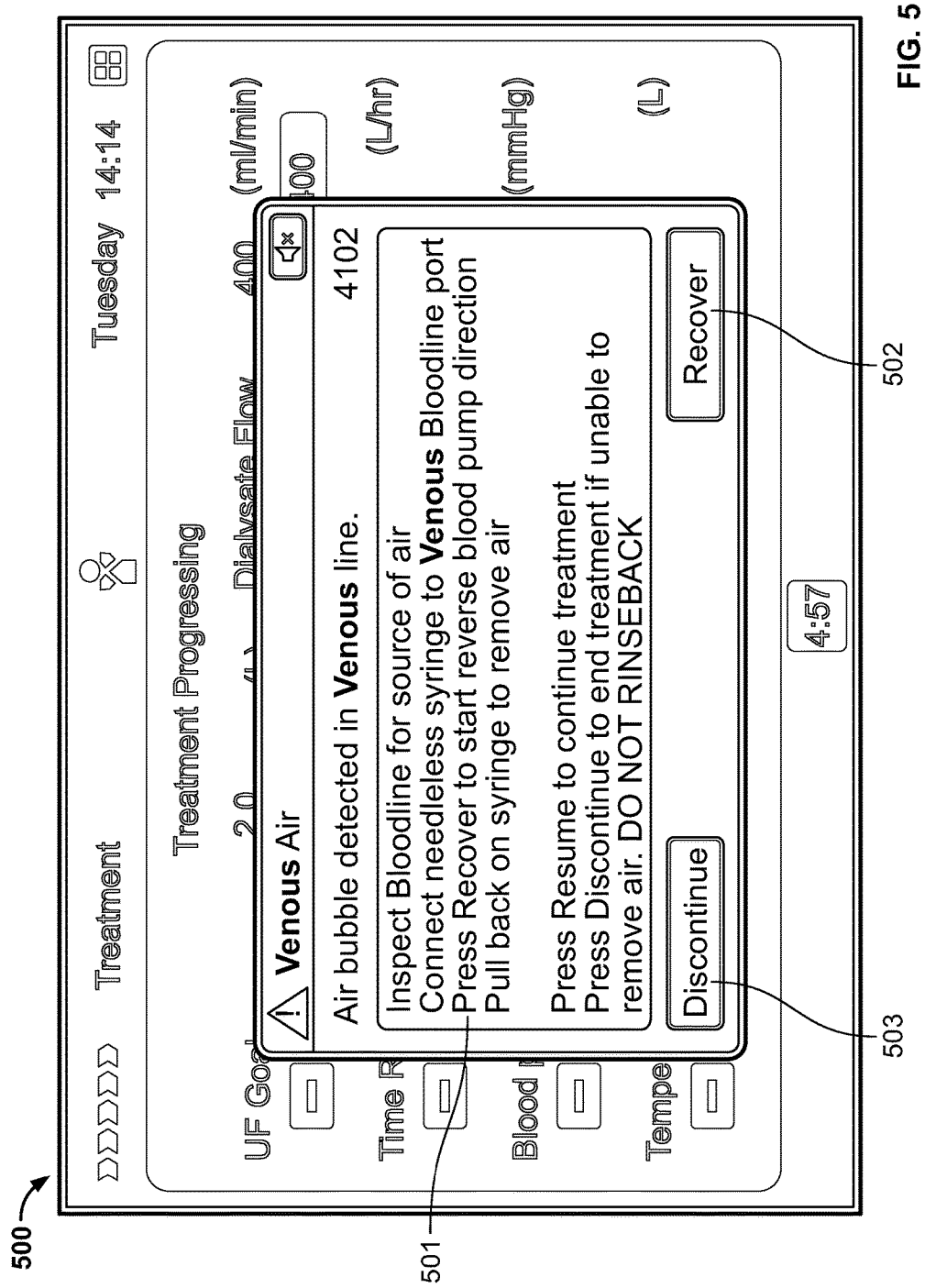
FIG. 5 shows an exemplary GUI screen displayed on the dialysis device when an air bubble is detected.

FIG. 5 shows an exemplary GUI screen 500 which is displayed on the dialysis device when an air bubble is detected and an alarm is issued. Screen 500 also optionally displays instructions 501 to guide the user to proceed further. Thus, the user may be asked to inspect the bloodline for air and connect a needleless syringe to the venous bloodline port. In one embodiment, the instructions are accompanied by a suitable graphic to illustrate where the requisite port is and how to connect the syringe for extraction.

In one embodiment, the GUI screen displays a "Recover" icon or button 502 to facilitate the process of air bubble removal. Referring to FIG. 4 and FIG. 5 simultaneously, when the user presses or touches the "Recover" button, the system controller issues a set of instructions causing the pump control to run the blood pump (shown in FIG. 4) in a reverse direction, in a direction opposing the conventional flow pathway, causing the blood from the venous line to flow back towards the dialyzer. As the fluid flows in a reverse direction, the air bubble is drawn close to the access point or port, which is located upstream towards the dialyzer. Once the air bubble is at the access port the user can pull back on the needleless syringe to remove the air, as per the instructions displayed on the GUI.

It may be noted that the GUI also provides the user also an option to "Discontinue" the hemodialysis treatment by pressing an icon or button 503, if the user is unable to remove the air bubble. In one embodiment, the system automatically runs the blood pump in a reverse direction, as soon as an air bubble is detected.

In one embodiment, when the user presses the "Recover" icon, the blood pump is run in the reverse direction, until the bubble reaches substantially close to the extraction point or port. In an embodiment, the pump is run in the reverse direction for a specified time period. Optionally, the specified time period is 12 seconds.

Figure 6:
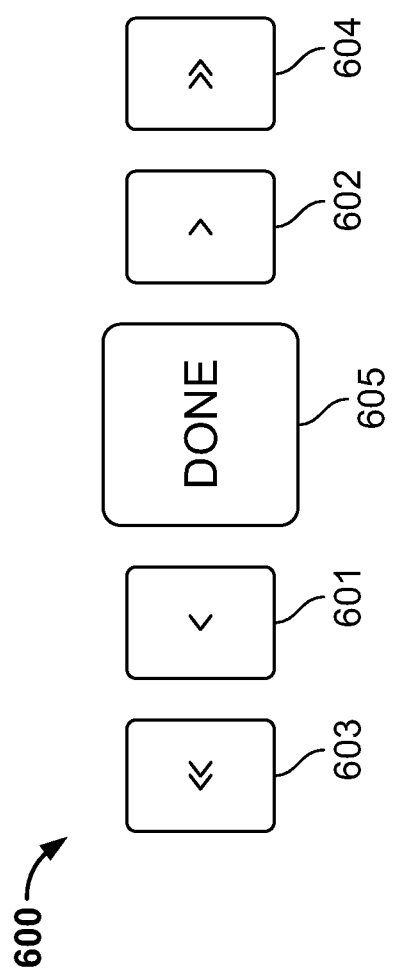
FIG. 6 illustrates an exemplary set of icons that is displayed on the GUI of the dialysis device, according to one embodiment.

As soon as the pump is stopped, in one embodiment, the GUI displays another set of icons to the user. FIG. 6 illustrates an exemplary set of icons that is displayed on the GUI screen according to one embodiment, when the pump stops running in the reverse direction.

Referring to FIG. 6, the exemplary set of icons 600 includes navigation buttons which, in one embodiment, represent movement such as reverse arrow "<" 601, forward arrow ">" 602, fast reverse arrow "<<" 603 and fast forward arrow ">>" 604. These buttons help the user to make incremental adjustments and precisely position the air bubble under the desired port. Thus, for example pressing the "<" button may allow the pump to run in the reverse direction such that the air bubble is moved a short distance (such as around 3 mm). In one embodiment, the motor is run at a defined and acceptable rate to the user. Similarly, the ">" 602 button may be used to run the pump such that the air bubble is moved a short distance (such as around 3 mm) in a forward direction. Still further in the example, navigation buttons "<<" 603 and ">>" 604 may be similarly used to run the pump and move the air bubble incrementally farther in the reverse or forward direction, but for a greater distance (such as around 6 mm). Also, the rate at which the air bubble moves by pressing any of the navigation buttons is a defined and acceptable rate for the user. It may also be noted that range of movement of air bubble on pressing a particular navigation button depends on the specific application and the type of dialysis system being used, and some embodiments may require more precise and fine control of the range of movement. In some embodiments, the range of incremental movement varies from 1 to 2 cm. In other embodiments, such as non-dialysis devices where the present mechanism may be employed, the range of movement may be as accurate as 1 to 2 mm. It may be noted that limiting the range of movement ensures that an air bubble does not move too far, and mitigates the risk of formation of more air bubbles.

It may be noted that symbols such as "<" or ">" are used here for simplicity and any symbols or words may be used for display on the GUI, so long as they can be easily comprehended by a user and serve the purpose of navigation for the air bubble.

In one embodiment, another button or icon is provided that allows a user to resume treatment after the air bubble has correctly been positioned. In the present example, this purpose is served by the "Done" button 605.

Figure 7:
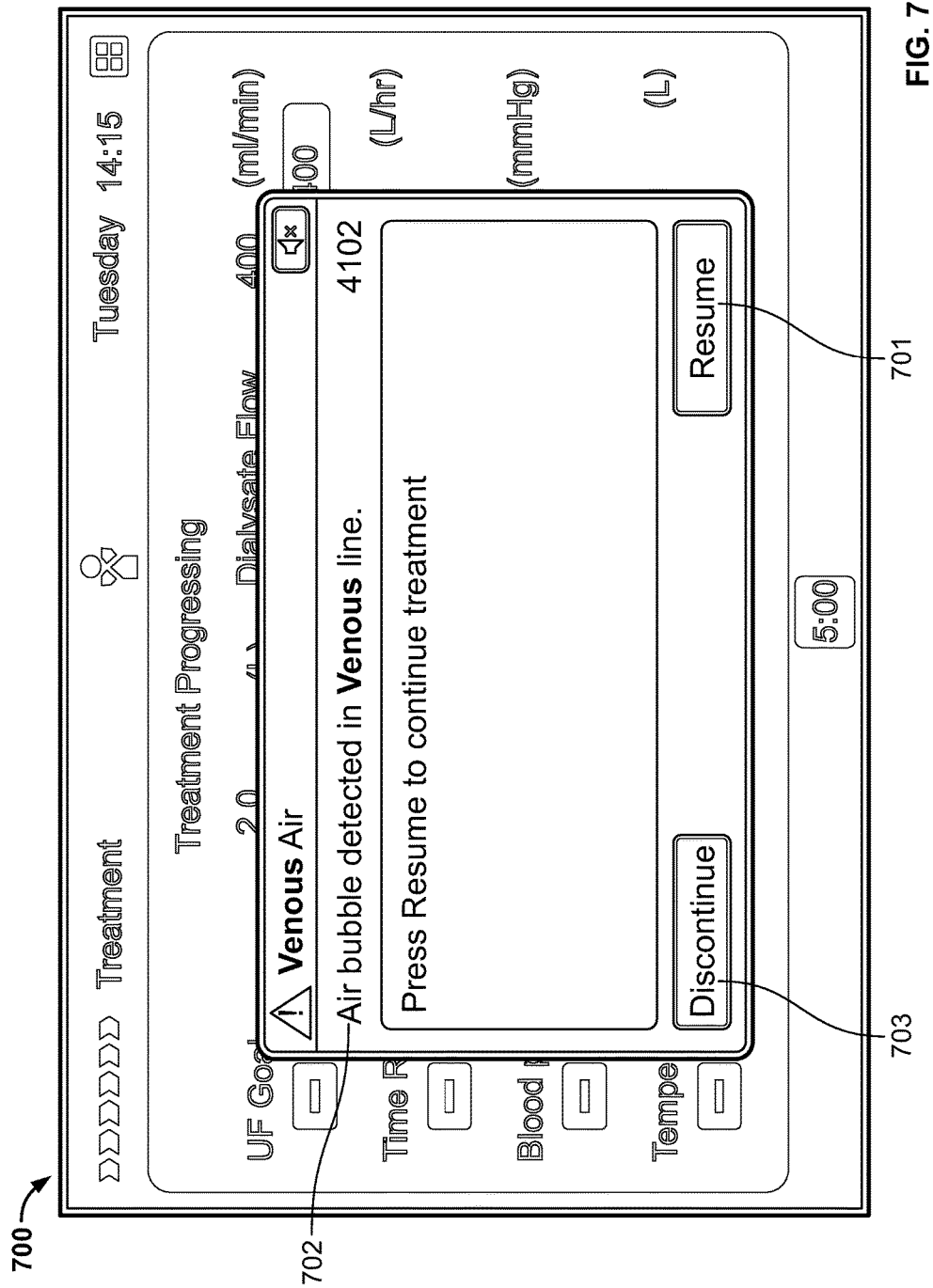
FIG. 7 illustrates another exemplary GUI screen displayed on the dialysis device.

For resuming treatment in one embodiment, the GUI displays another screen with the status of the air bubble, that is, whether the bubble has been removed. FIG. 7 displays one such exemplary GUI screen 700. Referring to FIG. 7, after the user safely extracts the air bubble from the access point, they can press the "Resume" button 701. Pressing the "Resume" button 701 indicates to the system that the air bubble is removed from the venous line and it changes the status 702 accordingly. If a user is unable to extract the air bubble, they can choose to discontinue treatment using an icon or button 703 provided for the purpose. A person of ordinary skill in the art would appreciate that in case the air bubble has not been removed properly at the designated port, it is detected again by the air bubble detector (as shown in FIG. 4).

FIG. 8 is a flowchart illustrating the process flow for air bubble detection and removal, according to one embodiment of the present specification. The steps in the flowchart are executed by the controller of the hemodialysis device. Referring to FIG. 8, when an air bubble in the venous line to the patient is detected in 801, a signal is sent by the detector to the controller, which then issues an immediate alarm to the user via GUI. This is shown in step 802. The GUI also displays instructions to the user regarding how to safely remove the air bubble. The user is given the option to choose "Recover" 803, which assists with air bubble removal or "Discontinue" 804, which stops the dialysis treatment (809). These options have been explained earlier with reference to FIG. 5. When the user chooses "Recover", the controller issues instructions to automatically run the blood pump in a reverse direction in order to place the air bubble near the extraction port. This is shown in 805. Subsequently, if required the user may incrementally adjust the position of the air bubble using navigation buttons provided on the GUI, as shown in step 806. In one embodiment, when the user presses a button for incremental adjustment, the pump is moved for a predetermined period of time, at a specific rate. This enables the movement of the bubble for a precise and specific distance. It may be noted that this mechanism eliminates the onus on the user to be precise. Even if the user presses a button too many times and moves the bubble too far ahead, they can use the reverse movement to move the bubble back if required.

Once the user is able to successfully extract the air bubble, assisted by the instructions provided by the GUI, and as determined in step 807, the user may choose to resume treatment, as shown in step 808. It may be noted that the method of extracting the air bubble employed in the present system comprises using a syringe attached to the port to pull out the bubble. This method is known in the art to work consistently across tubing sets, machines and users, when an air bubble is placed within a short distance, which in one embodiment, is approximately an inch from the extraction port. If however, the user is unable to extract the air bubble, they can choose to discontinue treatment, as shown in steps 807 and 809.

Thus, the system and method of present specification involves two main steps to correctly position the air bubble:

1) an automatic movement by the system to initially move the air bubble to a position estimated to be near the extraction port; and 2) a manual step where the user presses the forward/backward buttons, and repeats if required, to position the air bubble accurately in relation to the desired port.

In one embodiment, for the automatic movement in the first step, the pump is run at a specific rate for a specific period of time. It may be appreciated that the rate at which the pump runs needs to be slow enough such that the bubble cohesion is not broken and the bubble does not disintegrate or break up. The rate or speed of pump also depends on the dimensions and configuration of the tubing that the bubble will travel in. For example, if the tubing is rounded or looped near or around the port, slightly faster rate is allowable. In one embodiment, the operating rate of the pump ranges between 20-100 ml/min, for plastic tubing that is around ¼" thick, assuming that there is no looping in the tubing. It should further be appreciated that the pump should be run for a time sufficient to have the bubble travel from the bubble sensor to the extraction port in accordance with all of the aforementioned distances between the bubble sensor and the extraction port.

In one embodiment, upon activating the automatic movement or step movement of the pump, the pump is run for a first period of time of the order of 2-15 seconds, and at a rate of around 20-60 ml/min, and then terminates for a period of time. This allows positioning of the bubble sufficiently close to the port where it can be extracted by the user. It may be noted that the rate and the period of time for which the pump is run is selected depending on the dialysis circuit and to achieve a balance such that it is neither too slow such that the user gets impatient or annoyed, and neither too fast such that there is a risk the bubble disintegrating into microbubbles.

It may further be noted that particular tubing types may allow slightly faster rate for the pump to operate or may require it to be slower. For example, if the interior of the tubing is smooth, a faster rate can be used. A corrugated or rough interior on the other hand, may require slower rates in order to prevent the bubble from breaking up.

In one embodiment, the pump is only run in a reverse or backwards direction (opposite the direction of blood flow). In other embodiments, the pump is run in multiple movements. For example, the pump may be run backward for a period of time, then forward for a short time. This would help coalesce "micro-bubbles" surrounding or trailing the main bubble. One of ordinary skill in the art would appreciate that the sequence and number of forward/backward movements would depend on the application, and any combination of such movements may be used so long as they serve the purpose of the particular application. Further, the rate (speed) and duration of each movement may also be determined and customized, depending on the application.

In one embodiment, during the second step, the user is allowed to press the forward/back navigation buttons a limited number of times. This is to prevent the bubble from travelling back to the patient. It may be appreciated that the actual limit of the number of times a user can move the bubble forward or backward would depend on the configuration and geometry of the tubing. In one embodiment where tubing geometry is complex, a limit based on the detected bubble size is determined. Thus, for example, a larger or longer bubble has a lower number of forward/backward button presses allowed, to prevent a possibility of the tail end of the bubble making its way back into the patient.

Another factor in determining the number of times a user is allowed to move the bubble forward or backward is the original speed at which the pump was running, before it was stopped because of the bubble detection. For example, if the pump is running at a high speed and is abruptly stopped when an air bubble is detected, the bubble may break up into several micro-bubbles. In this case, a lower number of forward/backward movements are allowed, in order to prevent the micro-bubbles from entering the patient.

In one embodiment, for more sophisticated and demanding applications, additional sensors are employed along the tubing near the port to determine the rate and duration for which the pump is automatically run when an air bubble is detected. In one example, when the bubble passes the first sensor in the series, the pump is slowed down. This would allow, for example, for the micro-bubbles surrounding the main bubble to coalesce and also ensure the main bubble does not fragment from there on. The slower speed would also allow the next sensors in the series to more accurately detect the start of the bubble and thereby position it more accurately under the port.

As mentioned earlier, the incremental movements provided by the navigation buttons enable short runs of the pump. For example, pressing "<" moves the bubble by 1 cm along the tubing to the left and pressing "<<" would move it by 3 cm along the tubing to the left. The actual length of the movement (distance travelled by the air bubble) depends on the geometry of the tubing/port. For example, if the port is 20 cm in diameter, the 1 cm movement may need to be configured to a longer incremental movement that corresponds to each navigation button.

It may be appreciated that the length or duration of incremental movements associated with each navigation button also depends on "usability" or ease of operation for the user. For example, if pressing "<" moves the bubble by 1 cm and pressing "<<" moves it by 50 cm, that would make the process of precisely positioning the bubble very difficult and frustrating for the user. Thus it is important that the relative magnitudes of the movements associated with the navigation buttons are reasonable. In one embodiment, the present system maintains a ratio in the range of 1:2 to 1:4 for the short ("<") and large ("<<") distance movement of the air bubble enabled by navigation buttons. It may be appreciated that a ratio of less than 1:2 or more that 1:4 would make the process cumbersome for the user.

In one embodiment of the specification, the mechanism does not use arrows or navigation buttons such as "<". Instead, there is a single button representing a "Recover" function, explained above with reference to FIG. 5. In one embodiment, when the user presses the button, the system simply runs the pump in reverse direction for a specific period of time and at a specific rate. In one embodiment, the button is allowed to be pressed once.

In one embodiment, parameters such as specific rate and the specific period of time for which the pump is run on pressing the "Recover" button, are empirically determined depending upon the application. The rate or speed of the pump is chosen such that it moves the bubble quickly enough so that it is not frustratingly slow for the user, and yet not fast enough such that the bubble disintegrates while moving. In one embodiment, the time period for which the pump is run is determined based on the length of tube from the air bubble detector to the extraction port. Thus, for example if the total distance from the sensor that detected the bubble to the port is about 16 inches, then the time period for which the pump is run simply corresponds to how long it takes the pump to move a bubble for that distance. In one application involving a portable artificial kidney device, the pump is run for about 12 s at 40 ml/min. This duration and speed are empirically determined to be adequate to achieve the purpose of positioning the air bubble close to the extraction port for the given device configuration. In the given application, this moves the bubble to within an inch of the port.

FIG. 9 is a diagram of exemplary hardware architecture for one embodiment of the dialysis system. Referring to FIG. 9, the dialysis system comprises at least one processor or controller and a memory for storing programmatic instructions which, when executed, communicates with a software application layer 905. The software application layer 905 interfaces with a master controller 910 that is in data communication with a plurality of field programmable gate arrays responsible for controlling various pumps, sensors, and valves (Control FPGAs) 915 and in data communication with a plurality of field programmable gate arrays responsible for monitoring the operation of various pumps, sensors, and valves for failure states or states which exceed accepted operational parameters 920 (Safety FPGAs).

Control FPGAs 915 execute hardware instructions for controlling the operation of all system components, including pumps, sensors, and valves, and transmitting state information of the components to both the controller 910, which, in turn, processes the information and passes certain data for further processing and/or display to the application layer 905, and the Safety FPGAs 920, which monitor the state information for an alarm condition, such as an operational parameter exceeding or not meeting one or more predefined threshold values.

Where the Control FPGAs 915 generate data indicative of an alarm condition or generally indicative of a need to terminate or suspend operations, the controller 910 or application layer 905 may issue one or more commands to terminate operations. Independently, however, the Safety FPGAs 920 receive the data and may directly issue commands, or otherwise cause, the operation of one or more valves, pumps, or sensors to terminate, suspend, or otherwise change state. The Safety FPGAs 920 may do so after receiving data directly from the Control FPGAs 915 or independently if directly instructed by the controller 910 or directly instructed by the application layer 905. By having the Safety FPGAs directly receive data from the Control FPGAs 915 and instructions from the application layer 905 and controller 910, with no mediating layer in between, the system can effectuate a shutdown, suspension, or other modification in state in response to an alarm condition or user instructions more rapidly and reliably.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A portable dialysis system for conducting hemodialysis on a patient, the system comprising:
    a dialyzer;
    an arterial blood line for carrying blood from the patient;
    a blood pump for drawing blood from said arterial line and pumping it to the dialyzer;
    a venous blood line for carrying purified blood from said dialyzer to said patient;
    a pinch clamp to prevent air in said venous line from being returned to the patient;
    an air bubble detector positioned in said venous blood line for detecting an air bubble arising in said venous blood line, wherein the air bubble detector is positioned within a range of 10 to 20 cm upstream of said pinch clamp and within a range of 20 to 40 cm downstream of said dialyzer;
    an extraction port located within a range of 10 to 20 cm upstream of said air bubble detector and within a range of 10 to 20 cm downstream of said dialyzer in the venous blood line, said extraction port being adapted to remove the said air bubble; and
    a controller in communication with said air bubble detector and said blood pump, said controller configured to cause said blood pump to run in a reverse direction back toward said dialyzer when an air bubble is detected, such that the air bubble is moved upstream towards the extraction port.

2. The system of claim 1, wherein the blood pump is run in a reverse direction for a specified time period of the order of 2-15 seconds.

3. The system of claim 1 further comprising a display with a Graphical User Interface (GUI), wherein said Graphical User Interface is in communication with said controller.

4. The system of claim 3, wherein the GUI is configured to issue an alarm as soon as an air bubble is detected.

5. The system of claim 4, wherein the GUI is configured to provide an option to the user to discontinue hemodialysis treatment when an air bubble is detected.

6. The system of claim 3, wherein when an air bubble is detected, the GUI is configured to display instructions for a user to remove the air bubble.

7. The system of claim 3, wherein the GUI is configured to display a plurality of navigation buttons, wherein said plurality of navigation buttons are configured to enable a user to adjust a position of the air bubble for extraction from said extraction port.

8. The system of claim 7, wherein pressing at least one of said plurality of navigation buttons causes the blood pump to run in a forward or reverse direction, such that the air bubble is moved downstream or upstream towards the extraction port.

9. The system of claim 1, wherein said controller is configured to automatically run said blood pump in a reverse direction when an air bubble is detected.

10. The system of claim 1, wherein said controller is configured to operate said blood pump in a reverse direction on user input, when an air bubble is detected.

11. In a portable dialysis system for conducting hemodialysis on a patient, a method for removing an air bubble arising in a venous blood line, said method comprising:
    detecting the air bubble arising in the venous blood line using an air bubble detector;
    issuing an alarm to the patient using a graphical user interface;
    electronically prompting a user of the portable dialysis system to select between recovering the air bubble and discontinuing treatment; and
    electronically receiving a selection of at least one recovering the air bubble or discontinuing treatment, wherein based upon said received selection,
        causing a blood pump to run in a reverse direction such that the air bubble is placed close to an extraction port;
        receiving input to confirm that the air bubble is successfully extracted; and
        resuming hemodialysis treatment when the user confirms the air bubble is successfully extracted.

12. The method of claim 11 further comprising displaying a plurality of navigation buttons on said graphical user interface based upon electronically receiving the selection of recovering the air bubble.

13. The method of claim 12, wherein said at least one of said plurality of navigation buttons is configured to adjust a position of the air bubble for extraction from said extraction port.

14. The method of claim 12, wherein pressing a forward navigation button causes the blood pump to run in a forward direction such that the air bubble is moved downstream towards the extraction port.

15. The method of claim 12, wherein pressing a reverse navigation button causes the blood pump to run in a reverse direction such that the air bubble is moved upstream towards the extraction port.

16. The method of claim 11, wherein, upon running the blood pump in the reverse direction, the blood pump operates for a first period of time of the order of 2-15 seconds, and at a rate of around 20-60 ml/min.

* * * * *